(12) United States Patent
Ohlsson

(10) Patent No.: US 6,823,208 B2
(45) Date of Patent: Nov. 23, 2004

(54) INTERFACE UNIT FOR AN ELECTROPHYSIOLOGY MEASUREMENT SYSTEM

(75) Inventor: Thomas Ohlsson, Hasselby (SE)

(73) Assignee: Siemens Aktiengesellschaft, Münich (DE)

(*) Notice: Subject to any disclaimer, the term of this patent is extended or adjusted under 35 U.S.C. 154(b) by 5 days.

(21) Appl. No.: 09/843,987

(22) Filed: Apr. 27, 2001

(65) Prior Publication Data
US 2001/0056244 A1 Dec. 27, 2001

(30) Foreign Application Priority Data

May 29, 2000 (SE) .............................................. 0001999

(51) Int. Cl.⁷ .......................................... A61B 5/0402
(52) U.S. Cl. ..................................................... 600/509
(58) Field of Search ................................. 600/300, 301, 600/509, 522; 607/38; 361/809, 810; 73/866.5

(56) References Cited

U.S. PATENT DOCUMENTS

| | | | |
|---|---|---|---|
| 3,805,116 A | | 4/1974 | Nehmann |
| 4,695,955 A | | 9/1987 | Faisandier |
| 5,425,361 A | * | 6/1995 | Fenzlein et al. ............ 128/635 |
| 5,640,967 A | * | 6/1997 | Fine et al. ................... 128/710 |
| 5,669,393 A | * | 9/1997 | Faisandier ................... 128/710 |
| 5,776,057 A | * | 7/1998 | Swenson et al. ............ 600/301 |
| 5,821,405 A | | 10/1998 | Dickey et al. |
| 6,234,830 B1 | * | 5/2001 | Ensz et al. .................. 439/491 |
| 6,488,530 B2 | * | 12/2002 | Ohlsson ...................... 439/491 |

FOREIGN PATENT DOCUMENTS

| | | |
|---|---|---|
| DE | 866 536 | 7/1949 |
| EP | 0 614 678 | 9/1994 |
| WO | WO98/30145 | 7/1998 |

* cited by examiner

Primary Examiner—Jeffrey R. Jastrzab
Assistant Examiner—Frances P. Oropeza
(74) Attorney, Agent, or Firm—Schiff Hardin LLP

(57) ABSTRACT

An interface unit for an electrophysiology measurement system has a number of externally accessible electrical connectors, each connector for releasably mating with one of a number of wires from a combination of catheter-mounted sensors. A fixed configuration connector is provided in a fixed coupling to the connectors and is couplable to an electrophysiology monitoring system. The unit further has a signal generator, such as a suitably programmed EEPROM in combination with appropriate electrical circuitry mounted on an internally located printed circuit board, which generates an output signal containing information particular to and originating from the unit for use by the electrophysiology monitoring system.

14 Claims, 5 Drawing Sheets

| | ID |
|---|---|
| SETUP | |

| UNIT | LABEL |
|------|-------|
| BOX 1 | A1 |
| BOX 2 | A2 |
| BOX 3 | A3 |
| BOX 4 | A4 |

INTERFACE UNIT FOR AN ELECTROPHYSIOLOGY MEASUREMENT SYSTEM

BACKGROUND OF THE INVENTION

1. Field of the Invention

The present invention relates to an interface unit for use in an electrophysiology measurement system.

2. Description of the Prior Art

Electrophysiological measurement systems generally have a monitoring system for one or more of receiving, storing, processing and displaying signals from a number of patient interactive elements such as catheter-mounted intracardiac electrodes, surface ECG electrodes, blood parameter sensors, and similar physiological parameter sensors and an interface unit. The monitoring system often includes a switching unit by which measurements may be selectively made using different combinations of intracardiac electrode signals.

The interface unit is typically provided at bedside to receive the respective proximal ends of wires which are connected at their distal ends to the patient-interactive elements and provide for their electrical connection in a selectable optional manner to the switching unit of the monitoring system. The wires are received by the interface unit in releasable engagement with input terminals which, for the intracardiac electrodes are often arranged at the outer surface of the unit in a grid fashion, or so as to receive a multi-pin connector of a particular catheter. An output socket or permanent lead is provided for electrical connection to a connector in the monitoring system and comprises contacts connected to and arranged in a fixed correspondence with the input terminals. Which electrode wire connects to which terminal is dependent largely on the combination of catheters being used for a particular electrophysiology examination, the nature of that study and how the monitoring system is configured to receive the electrical signals.

The monitoring system may actually be provided with connectors for several interface units. Each connector then establishes electrical channels for signals from an associated interface unit by which the signals are supplied to a corresponding amplifier board where they are amplified and otherwise conditioned before they are operated on by the switching unit.

Before undertaking any electrophysiology examination, the measurement system must be initially set-up so that the correct catheter wires are mated with the correct terminals on the interface unit so that the correct measurements are made during the examination. To facilitate this set-up it is known to provide an interface unit wherein each terminal is permanently labeled in numerical sequence for identification purposes. Each wire of a particular catheter is usually provided with an identifying label by the manufacturer. Look-up tables can be constructed using these two sets of labels to indicate the wire/terminal mating configuration required for a particular examination. A wipe-clean surface may be available on the interface unit so that a label can be provided for each terminal used in the study which identifies the catheter electrode wire to be inserted according to the look-up table.

A problem may occur with this known electrophysiology measurement system when attempting to check if the correct wire is connected to the correct connector for a particular electrophysiology measurement. This is compounded by the fact that the monitoring system and the interface unit are often situated some distance apart and linked through a maze of wires.

To alleviate this problem it is known to provide an electrophysiology measurement system in which the monitoring system identifies itself to the interface unit. This is done by arranging for the monitoring system to generate an identifier on the interface unit, for example by lighting a colored diode or providing an alphanumeric code, which corresponds to an identifier for the connector to which the interface unit is connected. The user then can determine which unit is connected to which connector by a simple visual inspection of the identifier generated on the interface unit but not if the correct unit is connected to a connector. However, this solution does not readily assist the user in identifying whether the correct labels are provided on the correct interface unit.

Additionally, at least during the initial set-up of the monitoring system the wire/input terminal mating configuration of the interface unit necessary for a particular electrophysiology examination must be entered manually into the system and the correspondence checked with the actual configuration provided by the interface unit. This procedure often involves two persons, one at the interface unit and one at the monitoring system, one announcing the desired configuration to the other, who then either establishes the correct wire/terminal connection or enters the information into the monitoring system. This procedure typically needs to be repeated every time the electrophysiology examination is varied and provides an opportunity for user input error, which at best can cause errors in the data analysis and at worst can cause injury to the patient.

SUMMARY OF THE INVENTION

An object of the present invention is to provide an interface unit, and an electrophysiological measurement system employing such an interface unit, which simplifies set-up procedures and minimizes errors in set-up procedures.

The above object is achieved in accordance with the principles of the present invention in an interface unit, and in an electrophysiology measurement system employing such an interface unit, wherein the interface unit has a number of externally accessible female connectors which respectively releasably mate with male connectors of wires from a combination of catheter-mounted sensors in the electrophysiology measurement system, an arrangement for providing predetermined interconnections among said female connectors and being couplable to an electrophysiology monitoring system of the measurement system, and a signal generator connected to the arrangement, which generates an output signal containing information unique to and originating from the interface unit, the output signal being supplied to the electrophysiology monitoring system via the arrangement for use by the electrophysiology monitoring system.

By providing a unit which can generate an output signal containing information which can, for example, identify either or both the housing and a label layer (if provided) to an electrophysiology monitoring system, or provide set-up protocols for use by the system, then an automatic determination of the correct connections for a desired electrophysiology exam can be made automatically by the system and the potential for errors during a set-up procedure can at least be reduced, if not avoided.

Preferably, the interface unit has a removable label layer selectable from a library of label layers having a visible indication of a particular wire/connector mating configuration, permanently fixed at a surface thereof together with an element, such as a bar code label, useable to generate the output signal particular to the layer. This enables catheter wire connections to be rapidly established and varied whilst automatically providing information identifying the connections when the element is read by an appropriate reader, such as a conventional bar code reader.

The interface unit may provide the output signal which identifies to the electrophysiology monitoring system the electrophysiology study to be performed, by generating, for example, a coded reference to the exam or by generating a protocol useable to configure signal switches within the monitoring system in order to carry out the study. This further automates the set-up procedure and thereby reduces the potential for user input error.

DESCRIPTION OF THE DRAWINGS

FIG. 5 shows an automatically generated visual representation of interface unit/layer configuration for a desired electrophysiology study.

DESCRIPTION OF THE PREFERRED EMBODIMENTS

Figure 1:
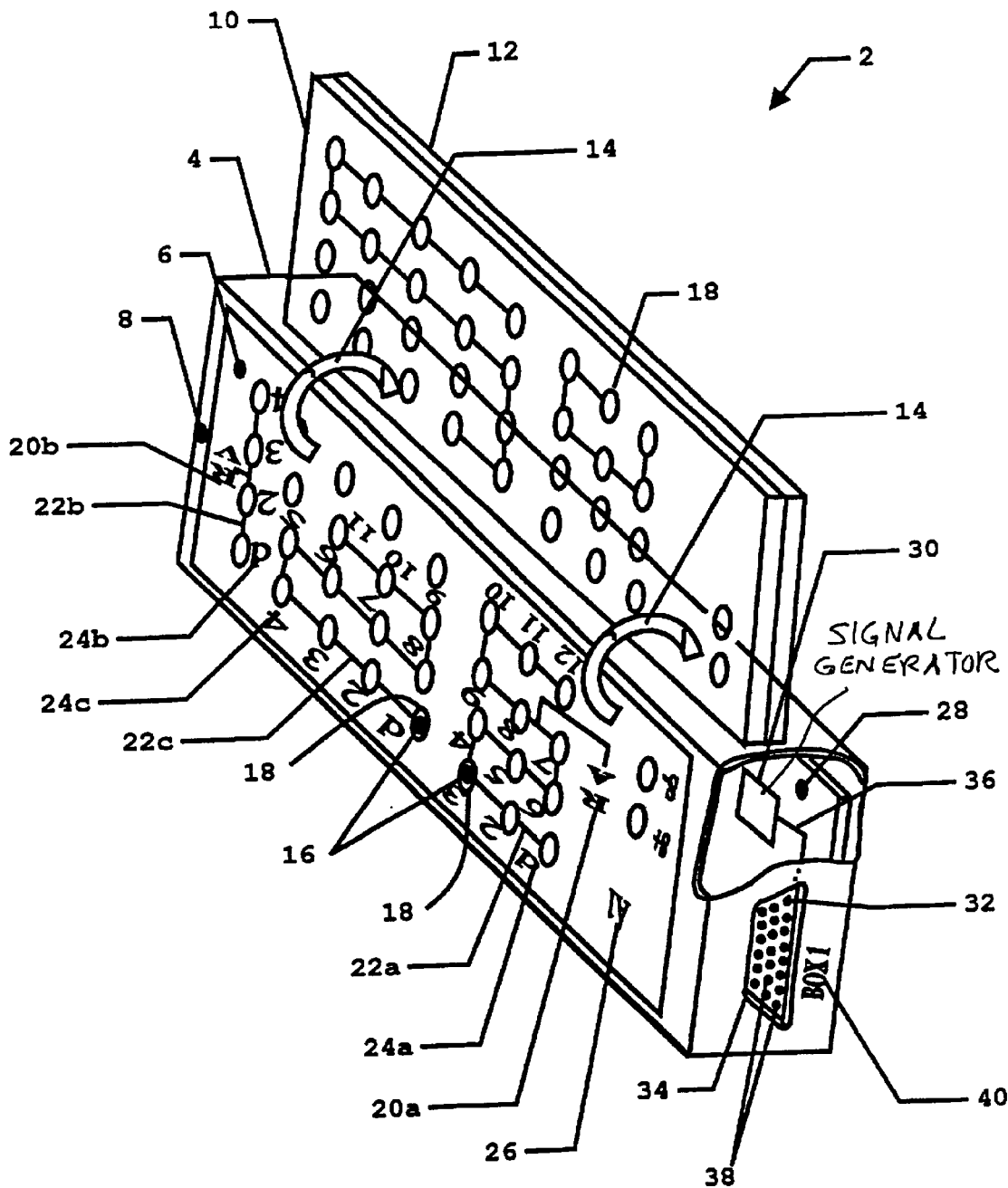
FIG. 1 is a perspective view of a first embodiment of an interface unit according to the present invention.

As shown in FIG. 1, an interface unit 2 has a housing 4 and a label layer 6 removably located at an outer surface 8 of the housing 4 and is selectable from a library of different label layers 10,12, all of which are releasably attached to the housing 4 by means of binding rings 14. A number of female connectors 16 are arranged in a grid in the surface 8 for releasable mating with male connectors which terminate sensor wires of a combination of catheters used in a particular electrophysiology exam (not shown) and register with through-holes 18 in a label layer 6,10,12 when the layer 6,10,12 is properly located on the surface 8 of the housing 4.

A fixed indication showing how the sensor wires of each catheter from the catheter combination is to be mated with the female connectors 16 is provided on each label layer 6,10,12. As illustrated in FIG. 1 for the removably located label layer 6 this indication may be catheter labels 20a and 20b ("RA", "RV"); linear demarcations 22a, 22b, 22c which group together those holes 18 (hence female connectors 16) which are intended to receive the wires belonging to an individual catheter of the combination; and for each of the individual catheter groupings 22a, 22b, 22c labels 24a, 24b, 24c associating the sensor wires of that catheter with the holes 18 (or connectors 16). By visibly grouping together the connectors 16 of a particular catheter in this way, the wire label convention (d,2,3 . . . ) normally used by a catheter manufacturer can be transferred to the label layers 6,10,12 with a reduced risk of confusion between different catheters. The label layers 6,10,12 also carry a human readable label layer identification code 26 to uniquely identify each label layer 6,10,12, and hence a particular catheter combination.

Thus, as an example for the embodiment of FIG. 1, it will be readily determined that for the currently located label layer 6—identified as "A1"—an electrophysiology exam can be carried out using any combination of the three catheters identified on the layer 6. It can be seen from this example that a first catheter, placed in the Right Atrium "RA", carries twelve sensor wires identified by the manufacturer with labels "d" to "12" which will mate with the twelve holes connected by the appropriate line 22a. A second is placed in the Right Ventricle "RV", carries four sensor wires identified by the manufacturer with labels "d" to "4" and will mate with the four holes connected by the appropriate line 22b. A third, placed elsewhere in the heart (no catheter identifier label being yet provided), carries eleven sensor wires identified by the manufacturer with labels "d" to "11" will mate with the eleven holes connected by the appropriate line 22c.

A printed circuit board (PCB) 28 is contained within the housing 4 and carries on it, among other things, a signal generator comprising a read-only-memory (ROM) 30, for example an (electrically) erasable-programmable ROM ((E)EPROM), which has an output connected to a pin 32 of a "D-type" connector 34, as illustrated by means of connecting line 36 in FIG. 1. Other pins, shown generally at 38, connect to an edge connector (not shown) on the PCB 28 which connects individual pins to individual female connectors 16 in a fixed relationship. The number of pins 38 may actually be less than the number of female connectors 16 if, for example, conventional signal multiplexing circuitry is included within the housing 4 so as to "connect" in a fixed manner individual connectors 16 to one or more pins 38.

This D-type connector 34 can readily be replaced by a permanent lead hard-wired to the PCB 28.

Figure 3:
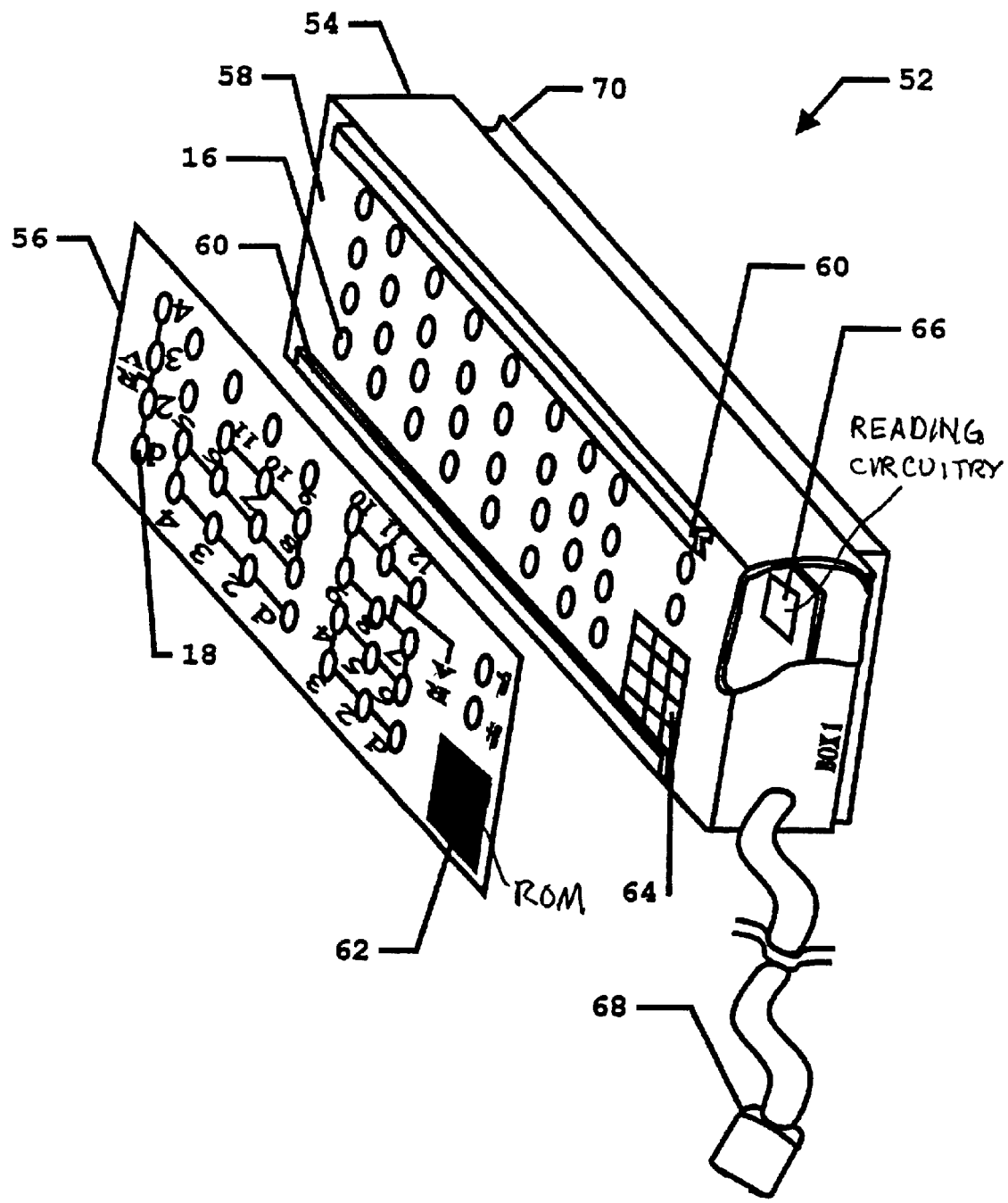
FIG. 3 is a perspective view of a third embodiment of an interface unit according to the present invention.

The ROM 30 is configured on the PCB 28 to provide an output signal containing information particular to the housing 4 at the pin 32 for receipt by an electrophysiology monitoring system (see FIG. 3). The information may, for example, be an identifier code particular to the housing 4 and which has a correspondence to a human readable housing identification code 40, if present. It will be apparent to those skilled in the art that if the interface unit 2 is modified so that the removable label layer 6 is permanently located on the surface 8 of the housing 2 (with the need for, among other things, the binding rings 14 and additional layers 10, 12 being removed) the signal provided by the ROM 30 will equally translate as information particular to the now fixed label layer 6, and hence to a unique catheter wire/connector combination provided by the unit 2.

It will be appreciated by those skilled in the art that the ROM 30, has a capacity to carry amounts of information in excess of a simple identification code and the information can be information useable by an electrophysiology monitoring system to automate its set-up. Such information can include a protocol for the wire/connector mating configuration which may then be used within an electrophysiology monitoring system to establish an appropriate switching configuration in order to achieve desired lead combinations or to select particular catheters necessary for a desired electrophysiology exam from the combination of catheters shown on the label layer 6.

Figure 2:
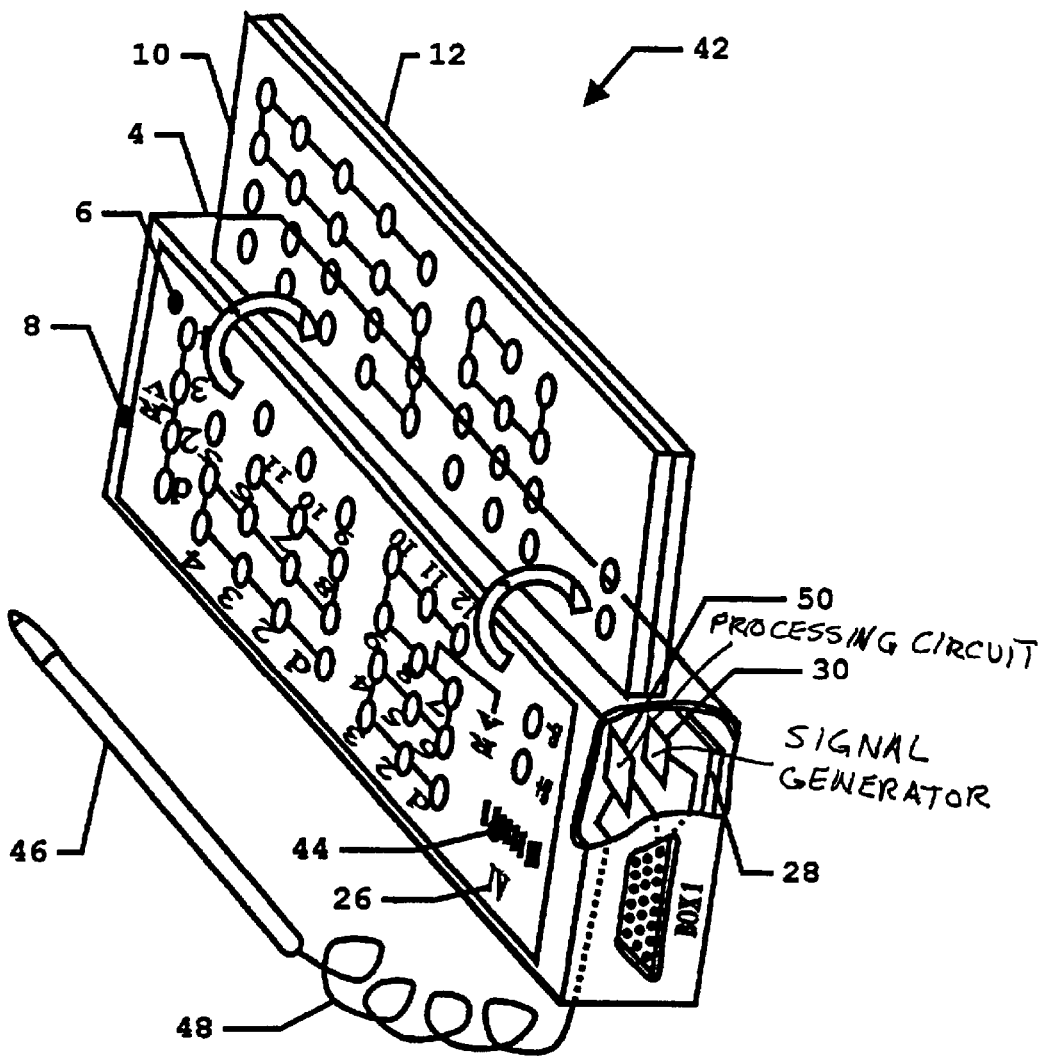
FIG. 2 is a perspective view of a second embodiment of an interface unit according to the present invention.

A second embodiment of an interface unit 42 according to the present invention is shown in FIG. 2 in which components common to this unit 42 and that unit 2 of FIG. 1 are identified by the same reference numerals. The interface unit 42 has a housing 4 and a number of label layers 6,10,12 which are each removably locatable on an outer surface 8 of the housing 4, as described with respect to the unit 2 of FIG. 1. Each layer 6,10,12 has, in addition or as an alternative to a human readable layer identification code 26, a machine readable code-carrying element, here shown as a bar code element 44 particular to the label layer 6,10,12. A bar code reader 46 is connected via a signal cable 48 to a dedicated processing circuit 50 which is located on a PCB 28 within the housing 4. The circuit 50 operates to convert the optical signal produced by the reader 46 from the code element 44 to an electrical signal. This electrical signal then can be supplied from the unit 2 via a pin 32 of a D-type connector (or lead wire of a hard-wired lead) to an electrophysiology monitoring system (see FIG. 4) where it uniquely identifies to the system the label layer 6 on the surface 8 of the housing 4 and which has a correspondence to the human readable layer identification code 26, if present.

As illustrated in FIG. 2, the interface unit 42 also may be provided with a ROM 30, such as described above with respect to FIG. 1, on the PCB 28 which provides the electrophysiology monitoring system with information particular to the housing 4, such as an identification code which has a correspondence to a human readable housing identification code 40, if present.

A third embodiment of an interface unit 52 according to the present invention is shown in FIG. 3 in which components common to this unit 42 and those units 2,42 of FIGS. 1 and 2 are identified by the same reference numerals. The interface unit 52 has a housing 54 and a label layer 56, selected from a number of label layers (not shown) dependent on a particular electrophysiology study to be performed. The layer 56 has a number of through holes 18 which correspond to a number of electrical connectors 16 when the layer 56 is correctly located at an outer surface 58 of the housing 54. To facilitate the correct location and to help retain the layer 56 on the surface 58, guides 60 may be provided which, in co-operation with the surface 58, establish channels within which edges of the layer 56 are to be received.

A ROM 62, such as an EEPROM, is located together with associated circuitry on the label layer 56 and contains information particular to the label layer 56. This information can include items which range from, for example, a layer identification code to protocols used to control the operation of an electrophysiology monitoring system to perform a particular electrophysiology study associated with the layer 56 and/or to present collected data in a particular manner.

A reading head 64 is located on the outer surface 58 of the housing 54 to establish electrical contact with the ROM 62 when the layer 56 is correctly located on the surface 58 and is connected to reading circuitry 66 located within the housing 54. The ROM 62, head 64 and associated circuitry 66 co-operate in a manner substantially similar to conventional "smart-card" technology to provide an output signal which contains the information stored in the ROM 62. It will be appreciated that other smart-card communication technology such as a wireless telemetry arrangement or a magnetic reader may be substituted for the electrical arrangement described above to provide for information communication between the label layer 56 and the housing 54.

External access to this output signal and to any sensor signals present at the connectors 16 is provided via a permanently connected lead 68.

A holder 70 is provided integral with the housing 54 in which label layers which are not used in the particular electrophysiology exam may be slidably retained.

Figure 4:
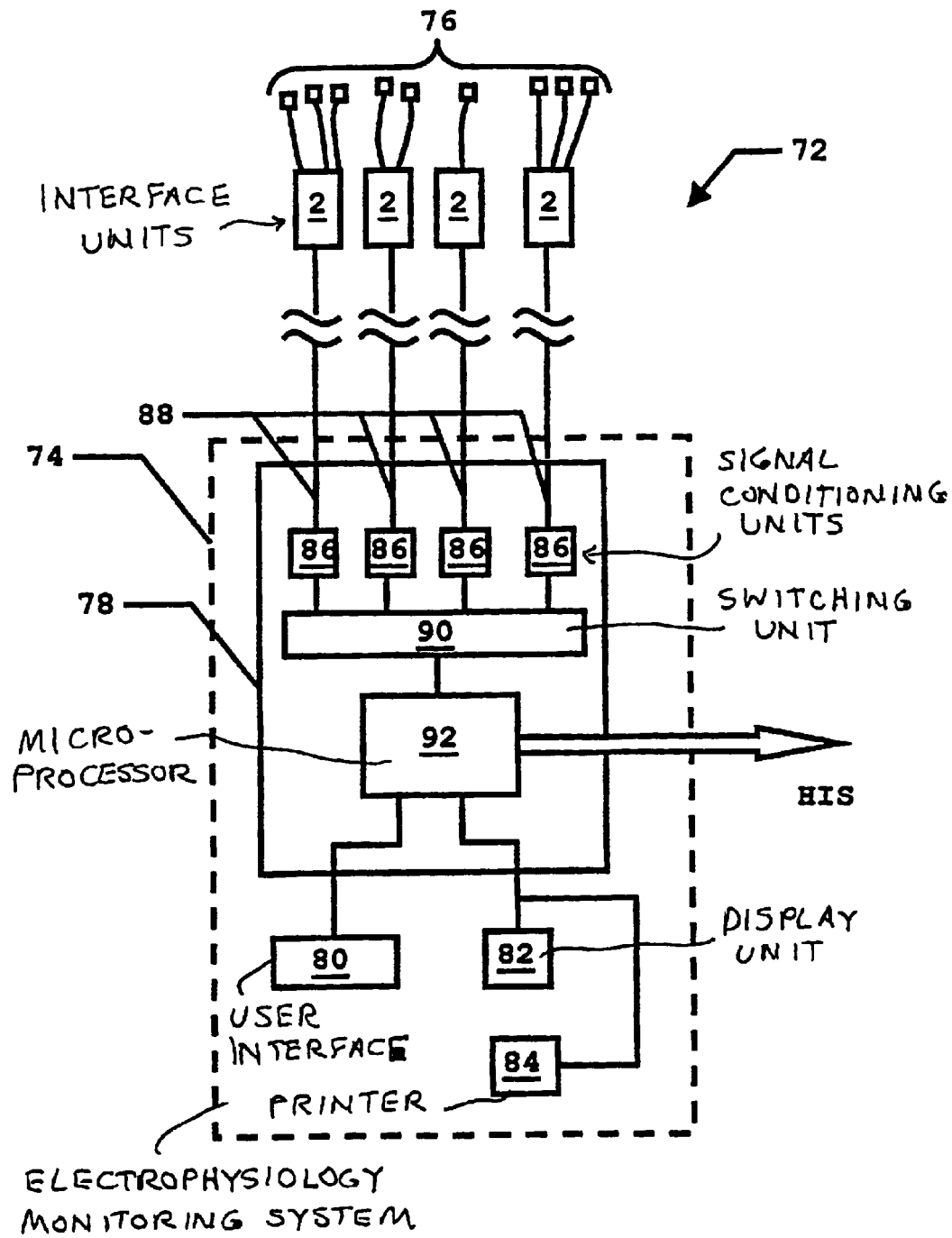
FIG. 4 is a block diagram of an electrophysiology measurement system according to the present invention.

A further embodiment of an electrophysiology measurement system 72 according to the present invention is shown in FIG. 4. The electrophysiology measurement system 72 has an electrophysiology monitoring system 74 and one or more (here four) interface units 2 of the present invention, each of which is connected to catheter-mounted sensors 76 required for a particular electrophysiology study. Each interface unit 2 has a different label layer 6,10,12 (see for example FIG. 1) at its outer surface and so each provides a different catheter wire/connector mating configuration.

The electrophysiology monitoring system 74 has a monitoring unit 78 which can receive information entered from each of the interface units 2 as well as from a user interface device 80 such as a keyboard and can send information to a hospital information system HIS as well as to a presentation device such as a visual display unit 82 and a printer 84.

More particularly, the monitoring unit 78 here has an array of conditioning units 86, each of which may be connected to a one of the interface units 2 by means of a dedicated externally accessible input socket having input connectors (not shown) corresponding to the pins 32, 38 of the D-connector 34 of a unit 2 and internal signal channels 88. The internal signal channels 88 could even be replaced by a single multiplexed connection to a single or to multiple conditioning units 86.

Signals from sensors 76 connected to a particular interface unit 2 pass to the inter-connected conditioning unit 86 within the monitoring unit 78 where it is amplified and otherwise conditioned, for example by filtering, before it is supplied to a switching unit 90. A suitably programmed microprocessor 92 operates to configure the switching unit 90 so as to selectively switch signals from all of the connected interface units 2 and combine them to produce so-called electrophysiology lead signals necessary to a particular electrophysiology study. Information required by the microprocessor 92 in order to correctly configure the switching unit 90 for the particular electrophysiology exam may be provided to the microprocessor 92 via the user input device 80 or additionally or alternatively via information passed from the signal generator 30 of the interface unit 2 as the output signal particular to the unit 2.

It will be appreciated by those skilled in the art that an embodiment of the present invention having the functionality of some or all of the individual components which form the monitoring unit 78 incorporated into the microprocessor 92 may be readily constructed while remaining within the scope of the invention.

These lead signals from the switching unit 90 can then be processed and analyzed within the microprocessor 92 in a manner dependent on the electrophysiology study, as is well known in the art.

Additionally or alternatively the signal generator 30 may provide an output which identifies the particular housing 4 in which it is contained. In the unit 2 of FIG. 1 the label layer 6 which is located on an outer surface 8 of the unit housing 4 is selectable from a library of label layers 6,10,12 according to a desired electrophysiology study to be undertaken (which may be identified to the microprocessor 92 by the user through the user interface device 80) and is identified by a human readable layer identification code 26. In this case the microprocessor 92 may be set-up by a user to retain in a memory a list of all layer identification codes; a list of those codes which identify label layers necessary for different electrophysiology studies; and a list linking the signal output by a particular identification means with the human readable housing identification code 40 of the particular housing. If it is necessary for a particular sensor signal combination to appear at a particular conditioning unit 86, a list linking the conditioning unit 64 and the label layer necessary to provide the combination also can be retained in the memory of the microprocessor 68.

When the signal from a signal generator 30 of each of the one or more connected interface units 2 is received at an inter-connected conditioning units 86 it is supplied to the microprocessor 92 together with a code identifying the particular conditioning unit 86 receiving the signal. The microprocessor 92 is programmed to then construct a lookup table which links the human readable box identification code 40 with a human readable layer identification code 26 necessary to provide the sensor signal combination from the identified interface unit 2 which is required at the interconnected conditioning unit 86 in order to carry out the desired electrophysiology exam. This lookup table 94 (see FIG. 4) may be presented on one or both of the display 82 and the printer 84 for use by a user to very simply manually verify that the correct label layer 6 is located on the correct interface unit 2 through a comparison of the visible layer code and box identification code combinations on the interface unit 2 with those presented in the table 94. Alternatively or additionally, each interface unit 2 may be provided with a display (not shown) which can be accessed and programmed by the microprocessor 92 of the monitoring unit 78 to present on the housing 4 the layer identification code corresponding to the code 26 of the necessary layer 6 for that unit 2.

If, as mentioned above with respect to FIG. 1, the label layer 6 is permanently located on the housing 4 of the interface unit then the output generated by the signal generator 30 also inherently identifies the label layer 6 and hence the associated wire/connector mating configuration. In this case the microprocessor 92 may be programmed to produce a discernable warning signal if the correct interface unit 2 is not connected to the correct conditioning unit 86 (dependent on the interface/conditioning unit combination required for the user indicated physiological study) or is missing.

Alternatively, the microprocessor 92 may be programmed to select the switch combination within the switching unit 90 dependent on the correct interface units 2 being present for the desired electrophysiology study, irrespective of how the conditioning units 86 inter-connect with the interface units 2.

The electrophysiology measurement system 72 of FIG. 3 may be modified by substituting the interface units 2 of FIG. 1 with interface units 42 or 52 of FIGS. 2 and 3, respectively. In this case the signal generator 44,46,50; 62,64,66 provides signals to the monitoring system 74 particular to the label layer 6;56 of each connected unit 42;52. The microprocessor 92 of the monitoring unit 78 may then be programmed to produce a sensible warning signal if the correct label layer 6 is not provided on an interface unit 42;52 connected to the correct conditioning unit 86 (dependent on the interface/conditioning unit combination required for the user indicated physiological study) or is missing.

The microprocessor 92 may be programmed to select the switch combination within the switching unit 90 dependent on the correct label layers 6; 56 being present for the desired electrophysiology study, irrespective of how the conditioning units 86 inter-connect with the interface units 42;52. Indeed the signal generator 44,46,50; 62,64,66 may be adapted to provide a switching protocol to the microprocessor 92 which is then used to establish the correct combination.

Furthermore, the switch combinations may be established so that particular catheters from the connected catheters are selected to achieve the correct catheter combination necessary for a particular electrophysiology study. Indeed the microprocessor 92 additionally or alternatively may be configured to set the switch combination of the switching unit 86 to carry out a particular electrophysiology study which is identified to the microprocessor 92 by the label layer specific information output from the signal generator 44,46,50; 62,64,66. In this manner the electrophysiology monitoring system 74 can be rapidly re-configured to perform any desired electrophysiology study simply by varying the label layers 6;56 located on one or more of the connected interface units 42; 52 and thereby vary the label layer specific information provided to the system 74. The use of appropriate layer specific information from the signal generator 44,46,50; 62,64,66 to control the set-up of the monitoring system 74 reduces the amount of human input data and thus the opportunity for data entry errors.

It will be appreciated by those skilled in the art that the microprocessor 92 may be programmed to modify the operation of the electrophysiology monitoring system 74 in many other ways dependent on the information received from the signal generator 44,46,50; 62,64,66 of each connected interface unit 42;52. The system 74 may, for example adapt the type and layout of information it records (either digitally on a digital storage medium or visually using a printer or visual display unit) in response to set-up protocols received from the signal generator 44,46,50; 62,64,66.

Although the embodiments of the electrophysiology measurement system presented above are described on the basis of a number of interface units, all being of the same type, an electrophysiology measurement system having only one interface unit or a combination of interface unit types according to the present invention connected to the electrophysiology monitoring system within which the microprocessor is adapted to respond accordingly will remain within the scope of the invention.

Although modifications and changes may be suggested by those skilled in the art, it is the intention of the inventor to embody within the patent warranted hereon all changes and modifications as reasonably and properly come within the scope of his contribution to the art.

I claim as my invention:

1. An interface unit for use with an electrophysiology measurement system having an electrophysiology monitoring system and a plurality of catheter-mounted sensors respectively connected to electrical connectors, said interface unit having an outer surface and comprising:

a plurality of externally accessible unit electrical connectors disposed at said outer surface, respectively adapted for releasably mating with a one of said sensor electrical connectors in a mating configuration;

an arrangement for producing predetermined interconnections among said unit connectors, said arrangement adapted for communicating with said electrophysiology monitoring system;

a signal generator connected to said arrangement which emits an output signal, adapted to be received by said electrophysiology monitoring system via said arrangement, containing information unique to and originating from said interface unit and designating said configuration, for use by said electrophysiology monitoring system; and at least one label layer placeable over said outer surface and carrying visible indications of said interconnections to form said configuration.

2. An interface unit as claimed in claim 1 further comprising a housing, and wherein said signal generator emits said output signal containing information unique to said housing.

3. An interface unit as claimed in claim 2 wherein said signal generator comprises a read-only memory containing said information unique to said housing.

4. An interface unit as claimed in claim 1 wherein said label layer is removably placeable on said outer surface.

5. An interface unit as claimed in claim 1 wherein said label layer is permanently fixed at said outer surface.

6. An interface unit as claimed in claim 1 wherein said signal generator comprises an element placeable on said outer surface together with said label layer and containing machine-readable information unique to said label layer and a reader arrangement for reading said machine-readable information from said element for generating said output signal.

7. An interface unit as claimed in claim 1 wherein said signal generator generates said output signal containing a protocol for said mating configuration among said sensor and unit connectors.

8. An interface unit as claimed in claim 1 wherein said signal generator emits said output signal containing at least a portion of an electrophysiology examination set-up protocol.

9. An electrophysiology measurement system comprising:
a plurality of catheter-mounted sensors respectively having sensor electrical connectors associated therewith;
a monitoring system for analyzing signals from said sensors; and
at least one interface unit connected between said sensors and said monitoring system, said interface unit having an outer surface and a plurality of unit electrical connectors disposed at said outer surface, respectively receiving a one of said sensor connectors in a mating configuration and containing an arrangement defining interconnections among said unit connectors, said arrangement being in communication with said monitoring system, and said interface unit further having a signal generator connected to said arrangement for generating an output signal unique to and originating from the interface unit, designating said configuration and being supplied to the monitoring system via said arrangement, said output signal modifying operation of said monitoring system dependent on said information, and a label layer, placeable on said outer surface, carrying a permanently fixed visible indication of said mating configuration and a humanly readable layer identification code.

10. An electrophysiology measurement system as claimed in claim 9 comprising a housing having a human readable housing identification code, and wherein said signal generator generates said output signal unique to said housing, and wherein said monitoring system has a data presentation device and a processor with label layer identification codes stored therein for predetermined electrophysiology examinations, said processor modifying operation of said monitoring system to present a layer identification code and a housing identification code protocol on said presentation device for a selected one of said examinations.

11. An electrophysiology measurement system as claimed in claim 10 wherein said signal generator generates said output signal also unique to said label layer, and wherein said electrophysiology monitoring system has a processor with an indication of at least one label layer stored therein for each of a number of different predetermined electrophysiology examinations, and wherein said processor compares the label layer identified in said output signal with an indication for a selected electrophysiology study, and modifies operation of said monitoring system dependent on a result of the comparison.

12. An electrophysiology measurement system as claimed in claim 9 wherein said signal generator generates an output signal containing at least a portion of an electrophysiology examination set-up protocol, and wherein said monitoring system has a processor which receives said set-up protocol and modifies operation of said monitoring system in accordance with said protocol.

13. An electrophysiology measurement system as claimed in claim 12 wherein said monitoring system comprises a signal switching unit having switch settings controllable by said processor, and wherein said set-up protocol contains information for use by said processor to vary said switch settings dependent on said examination.

14. An electrophysiology measurement system as claimed in claim 12 wherein said set-up protocol contains information for use by said processor for varying at least one of a presentation format and a type of study data recorded by said monitoring system.

* * * * *